United States Patent [19]

Zask et al.

[11] Patent Number: 5,236,941
[45] Date of Patent: Aug. 17, 1993

[54] 5-(2-HYDROXY-1-ARYLETHYLIDENE)- AND 5-(2-OXO-1-ARYLETHYLIDENE)-2,4-THIAZOLIDINEDIONES AND DERIVATIVES THEREOF

[75] Inventors: Arie Zask, New York, N.Y.; Ivo L. Jirkovsky, Plainsboro, N.J.

[73] Assignee: American Home Products Corporation, New York, N.Y.

[21] Appl. No.: 906,331

[22] Filed: Jun. 30, 1992

[51] Int. Cl.$^5$ .................. C07D 277/34; A61K 31/425
[52] U.S. Cl. ...................................... 514/369; 548/183
[58] Field of Search ........................ 548/183; 514/369

[56] References Cited

U.S. PATENT DOCUMENTS

| 4,738,972 | 4/1988 | Eggler et al. | 514/314 |
| 4,997,948 | 3/1991 | Zask et al. | 548/183 |
| 5,061,717 | 10/1991 | Clark et al. | 514/342 |
| 5,068,342 | 11/1991 | Zask et al. | 548/183 |
| 5,116,855 | 5/1992 | Inoue | 514/369 |
| 5,120,754 | 6/1992 | Clark et al. | 415/369 |

FOREIGN PATENT DOCUMENTS 0177353 10/1985 European Pat. Off. .
0332331 2/1989 European Pat. Off. .

OTHER PUBLICATIONS

Omar et al., Bull. Chem, Soc. Jpn., 64, 750–52 (1991).
Salama et al., Alex. J. Pharm. Sci. 4(1), 44–46 (1990).
Zask et al., J. Med. Chem. 33, 1418–23 (1990).
Yoshioka, et al., J. Med. Chem. 32, 421–28 (1989).
Fujita, et al., Diabetes 32, 804–810 (1983).

Primary Examiner—Robert Gerstl
Attorney, Agent, or Firm—R. F. Boswell, Jr.

[57] ABSTRACT 5-(2-Hydroxy-1-phenyl (or-1-naphthalenyl)ethylidene) and 5-(2-oxo-1-phenyl (or 1-naphthalenyl)ethylidene)-2,4-thiazolidinediones and derivatives thereof are useful in lowering blood glucose levels in a hyperglycemic laboratory animal model and are thus useful in the treatment of diabetes mellitus.

14 Claims, No Drawings

5-(2-HYDROXY-1-ARYLETHYLIDENE)- AND 5-(2-OXO-1-ARYLETHYLIDENE)-2,4-THIAZOLIDINEDIONES AND DERIVATIVES THEREOF

FIELD OF INVENTION

This invention relates to novel 5-(2-hydroxy-1-arylethylidene) and 5-(2-oxo-1-arylethylidene)-2,4-thiazolidinedione derivatives and pharmaceutically acceptable cationic salts thereof, a process for their preparation, and to their blood glucose lowering actions and their use in the treatment of diabetes mellitus.

BACKGROUND OF THE INVENTION

Diabetes mellitus is a syndrome characterized by abnormal insulin production, increased urinary output and elevated blood glucose levels. There are two major subclasses of diabetes mellitus. One is the insulin-dependent diabetes mellitus (IDDM or Type I), formerly referred to as juvenile onset diabetes since it was evident early in life, and non-insulin dependent diabetes mellitus (NIDDM or Type II), often referred to as maturity-onset diabetes. Exogenous insulin by injection is used clinically to control diabetes but suffers from several drawbacks. Insulin is a protein and thus cannot be taken orally due to digestion and degradation but must be injected. It is not always possible to attain good control of blood sugar levels by insulin administration. Insulin resistance sometimes occurs requiring much higher doses of insulin than normal. Another shortcoming of insulin is that while it may control hormonal abnormalities, it does not always prevent the occurrence of complications such as neuropathy, retinopathy, glomerulosclerosis, or cardiovascular disorders.

Orally effective antihyperglycemic agents are used to reduce blood glucose levels and to reduce damage to the nervous, retinal, renal or vascular systems through mechanisms affecting glucose metabolism. Such agents act in a variety of different mechanisms including inhibition of fatty acid oxidation, α-glycosidase inhibition, antagonism of $\alpha_2$-receptors and inhibition of gluconeogenesis. Two classes of compounds have predominated: the biguanides as represented by phenformin and the sulfonylureas as represented by tolbutamide (Orinase ®). A third class of compounds which has shown antihyperglycemic activity are thiazolidinediones of which ciglitazone is the prototype. Ciglitazone suppresses the symptoms of diabetes-hyperglycemia, hypertriglyceridemia and hyperinsulinemia [Diabetes 32, 804–10 (1983)].

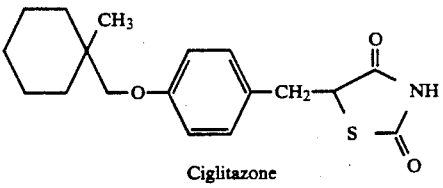

Ciglitazone

Yoshioka et al., J. Med. Chem. 32, 421–428 (1989) describe compounds where elements of Vitamin E, a potent antioxidant, and ciglitazone are combined that are useful for treating angiopathy (hyperlipidemia, diabetes and/or diabetic complications). These compounds have the formula:

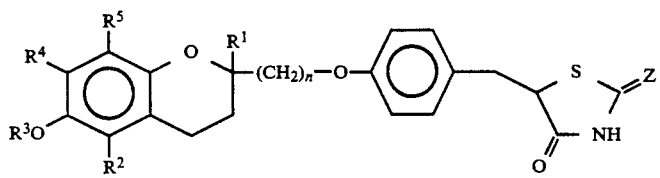

where $R^3$ is H, acyl or aroyl; $R^1$ and $R^2$ are H or lower alkyl, $R^4$ is H, lower alkyl or lower alkoxy; $R^5$ is lower alkyl or alkoxy, n is 1 or 2 and Z is O or NH.

Antihyperglycemic thiazolidinediones disclosed in our U.S. Pat. Nos. 4,997,948 and 5,068,342 and J. Med. Chem. 33(5), 1418-23 (1990) are represented by the following basic formulas:

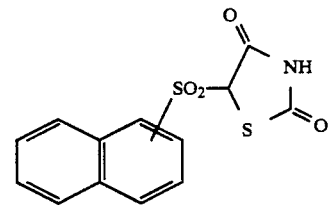

or

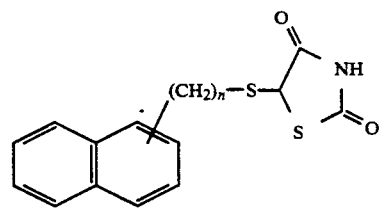

The synthesis of 5-(benzoylmethylidene)-2,4-thiazolidinediones via a 2-thioxo-4-thiazolidinone intermediate is reported in Bull. Chem. Soc. Jpn. 64(2), 750–752 (1991). The synthesis and in vitro antimicrobial evaluation of 5-(benzylmethylidene)-2,4-thiazolidinediones and 3-(benzoylmethyl-5-benzoylmethylidene)-2,4-thiazolidinediones is described in Alex. J. Pharm. Sci., 4(1), 44–46 (1990). U.S. Pat. No. 4,738,972 discloses hypoglycemic thiazolidinediones of the formula:

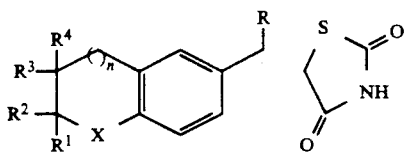

where X is —CH$_2$—, —CO—, —CHOH—, or —NR$^5$— and R is H, methyl or ethyl.

The European patent application 0332331A2 discloses hypoglycemic thiazolidine-2,4-diones which have the formula:

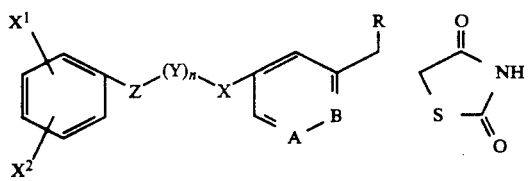

where either A or B is N and the other is —CH—, X is —S—, —SO—, —SO$_2$—, —CH$_2$—, —CHOH—, or —CO—; n is 0 or 1, Y is CHR$^1$ or NR$^2$ and Z is —CHR$^3$—, —CH$_2$CH$_2$—, —CH=CH—,

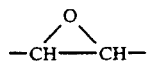

—OCH$_2$—, —SCH$_2$—, —SOCH$_2$—, or —SO$_2$CH$_2$—; and R, R$^1$, R$^2$, and R$^3$ are H or methyl. The dotted line in the above formula represents an optional bond.

The European Patent Application 0 177353A discloses 5-(4-substituted benzylidene)-2,4-thiazolidinediones which have blood glucose and lipid lowering activity useful for treating hyperlipidemia and diabetes.

Compounds of the present invention may thus be useful in the prevention and/or treatment of diabetic complications and as antihyperlipidemia and antihyperinsulinemic agents.

SUMMARY OF THE INVENTION

The compounds of this invention which are useful in the treatment of diabetes mellitus through their blood glucose lowering actions have the structure of general formula I

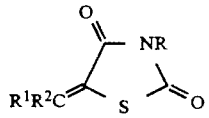

wherein:
R is H or lower alkyl,
R$^1$ is phenyl, 2,3-dichlorophenyl, 1-naphthalenyl or 5-methyl-1-naphthalenyl;
R$^2$ is R$^3$-X- where X is —CO— or —CHOR$^4$—and when X is —CHOR$^4$-, R$^3$ is H, loweralkyl, or aryl where aryl is phenyl or naphthalenyl optionally substituted by halogen, lower alkyl or lower alkoxy and when X is —CO—, R$^3$ is H;
R$^4$ is H or methyl;
or a solvate or a pharmaceutically acceptable cationic salt thereof;

and R$^1$ and R$^2$ may be in the E or Z configuration with respect to the 2,4-thiazolidinedione ring.

Under the definitions of terms in Formula I, lower alkyl is C$_1$-C$_6$ alkyl (straight and branched chain), lower alkoxy is -O-lower alkyl, and halogen is selected from fluorine, chlorine, bromine or iodine. The free valence of naphthalenyl is at either position 1 or 2.

The preferred compounds of this invention are those where R is H or methyl and R$^3$ is H, methyl, or phenyl.

The blood glucose lowering activity of the compounds of formulas I of this invention were demonstrated in experiments using diabectic (db/db) mice. The db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia.

DETAILED DESCRIPTION OF THE INVENTION

The compounds of this invention are prepared by reaction of dilithio-2,4-thiazolidinedione (J. Med. Chem. 33, 1418 (1990), U.S. Pat. Nos. 4,997,948 and 5,068,342) with an α-haloketone where R$^1$ and R$^3$ are as previously defined is reacted with an appropriate α-haloketone as shown in Scheme I.

Only one of the two possible configurations is represented in Schemes I-V. Under Scheme I, when R$^3$ is H only the E isomer is observed. When R$^3$ is other than H, a mixture of E and Z isomers is observed.

Scheme I

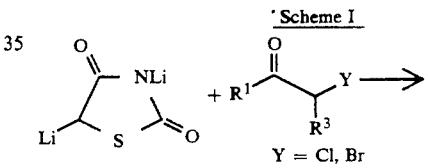

The Formula I aldehydes (X=—CO—, R$^3$=H) are obtained by oxidation of the corresponding alcohol (Scheme II) using Jones reagent.

Scheme II

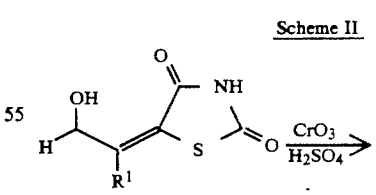

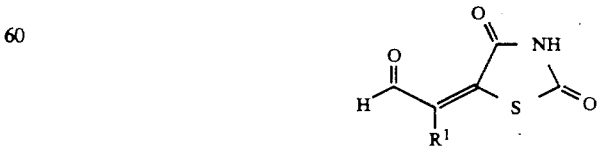

As an alternative procedure to Scheme I, Formula I compounds where R$^3$ is lower alkyl or aryl can be obtained by reaction of the aldehyde obtained in Scheme II with an appropriate Grignard or lithium reagent as shown in Scheme III.

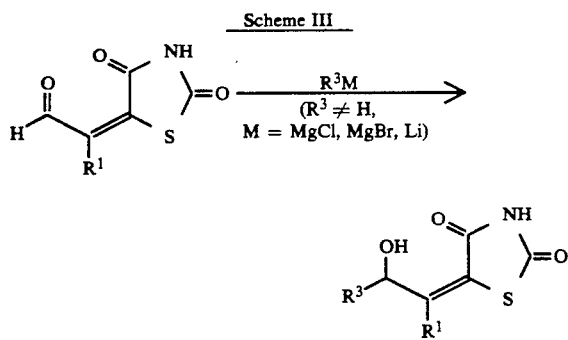

Formula I compounds where R is lower alkyl, illustratively methyl, can be prepared as outlined in Scheme IV.

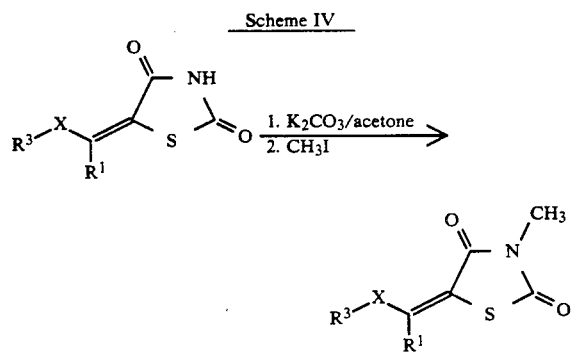

Formula I compounds where $R^4$ is methyl can be prepared according to the steps outlined in Scheme V. Where R is H, protection of the nitrogen atom at position 3 is required with a protecting group such as trimethylsilylethoxymethyl which can be readily removed.

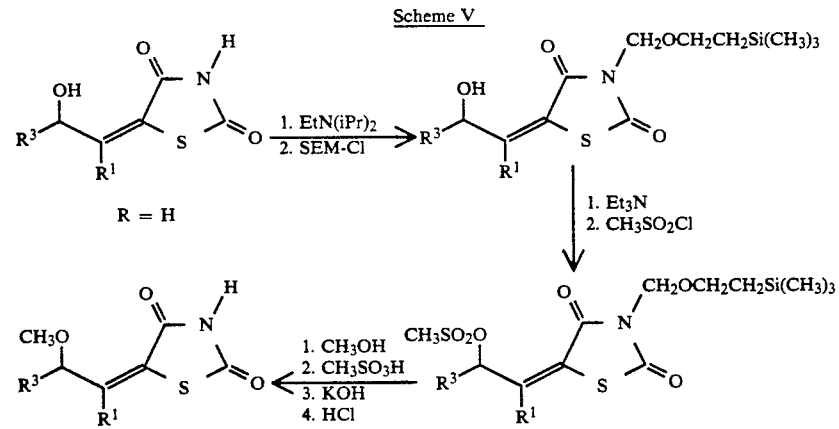

SALTS

The compounds of formula I form cationic salts with suitable therapeutically acceptable inorganic and organic bases. These derived salts posses the same activity as their parent acid and are included within the scope of this invention. Suitable inorganic bases to form these salts include, for example, the hydroxides, carbonates or bicarbonates of the therapeutically acceptable alkali metals or alkaline earth metals such as sodium, potassium, magnesium, calcium and the like. Suitable organic bases include amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol), procaine, etc. Furthermore, there may be mentioned the quarternary salts, for example, the tetralkyl (e.g. tetramethyl), alkyl-alkanol (e.g. methyltriethanol) and cyclic (e.g. N,N-dimethylmorpholine) ammonium salts. In principle, however, there can be used all the ammonium salts which are physiologically compatible.

Transformations to the corresponding salts are readily carried out by reacting the acid form of the compounds of formula I with an appropriate base, usually one equivalent, in a co-solvent. The salt is isolated by concentration to dryness or by adding of a non-solvent. For example, in the case of inorganic salts, it is preferred to dissolve the acid of Formula I in water containing a hydroxide, carbonate or bicarbonate corresponding the the inorganic salt desired. Evaporation of the solution or addition of a water-miscible solvent of more moderate polarity, for example, a lower alkanol such as butanol, or a lower alkanone such as ethyl methyl ketone, gives the solid inorganic salt. In the case of an amine salt, it is preferred to use a cosolvent of moderate or low polarity such as ethanol, ethyl acetate and benzene. Evaporation of the solvent or addition of a miscible diluent of lower polarity such as benzene or n-hexane gives the solid salt. Quaternary ammonium salts may be prepared by mixing the acid of formula I with a quarternary ammonium hydroxide in water solution followed by evaporation of the water.

The following specific examples are included for illustrative purposes and should not be considered as limiting the scope of this disclosure in any way. All starting materials are either commercially available or can be prepared by standard procedures known to one skilled in the art.

EXAMPLE 1

5-[2-Hydroxy-1-(1-naphthalenyl)ethylidene]-2,4-thiazolidinedione

To a solution of 2,4-thiazolidinedione (1.47 g, 12.6 mmol) in tetrahydrofuran (75 ml) at −78° C. was added n-butyllithium (17.3 mL, 27.6 mmol, 1.6M). The resulting white heterogeneous mixture was stirred at 78° C. for 1 h then treated with a solution of 2-bromo-1-(naphthalen-1-yl)ethanone (3.12 g, 12.6 mmol) in tetrahydrofuran (35 mL). After 1 h at −78° C., the reaction mixture was allowed to warm to 25° C. After 2 h excess solid ammonium chloride was added. The mixture was then partitioned between 5% aqueous sulfuric acid and chloroform. The aqueous phase was washed an additional two times with chloroform and the organic phases were then combined and dried over magnesium sulfate. Concentration in vacuo gave an orange oil (4.66 g). Flash chromatography (300 g silica gel. pretreated with 2% $H_3PO_4$/methanol; chloroform) gave the E-isomer of the title compound as a yellow oil (2.15 g) which was further purified by reverse phase chromatography (25 g $C_{18}$ silica gel, methanol/brine). Crystals (1.82 g, 51%) were obtained which were recrystallized from methanol/$H_2O$ to give the analytically pure product (1.2 g).

m.p. 169°-170° C.

IR (KBr): 3460 (bd), 3130 (m), 3030 (bd), 1733 (s), 1700 (s), 1325 (s), 1170 (m), 775 (s) cm$^{-1}$.

MS (EI) m/e (relative intensity): 285 (M$^+$,50), 256 (25), 242 (5), 196 (33), 155 (29), 153 (56), 152 (100), 128 (55), 127 (13).

$^1$H NMR (DMSO-d$_6$, 200 MHz): δ 5.02 (s, 2H, —CH$_2$—), 7.34-8.01 (m, 7H, ArH) Analysis calculated ($C_{15}H_{11}NO_3S$): C, 63.15; H, 3.86; N, 4.91. Found: C, 62.77; H, 4.12; N, 4.80.

EXAMPLE 2

5-[2-Hydroxy-1-(5-methylnaphthalen-1-yl)ethylidene]-2,4-thiazolidinedione.

Following the procedure of Example 1, the E-isomer of the title compound was prepared from 2,4-thiazolidinedione and 2-bromo-1-(5-methylnaphthalen-1-yl)ethanone.

m.p. 160°-161° C.

IR (KBr): 3435 (bd), 1731 (s), 1685 (s), 1608 (m), 1324 (s), 781 (s) cm$^{-1}$.

MS (EI) m/e (relative intensity): 299 (M$^+$, 96), 270 (30), 210 (100), 197 (37), 165 (63), 152 (50).

$^1$H NMR (CDCl$_3$, 400 MHz) δ 2.75 (s, 3H, CH$_3$), 4.21 (dd, J=6.9, 8.6 Hz, 1H. —OH), 4.77 (dd, J=8.7, 14.7 Hz, 1H, —CHH—), 4.88 (dd, J=6.8, 14.7 Hz, 1H, —CHH—), 7.35-8.15 (m, 6H, ArH).

Analysis Calculated ($C_{16}H_{13}NO_3S$): C, 64.17; H, 4.34; N, 4.68. Found: C, 63.41; H, 4.49; N, 4.54.

EXAMPLE 3

5-[2-Oxo-1-(1-naphthalenyl)ethylidene]-2,4-thiazolidinedione

To a solution of 5-[2-hydroxy-1-(1-naphthalenyl)ethylidene]-2,4-thiazolidinedione (10.13 g, 35.5 mmol) in acetone (250 mL) at 0° C. was added Jones reagent (8N, 10.26 mL, 82 mmol). After 30 min 2-propanol (10 mL) was added. The reaction mixture was filtered and concentrated in vacuo. The resulting oil was taken up in ether and washed with water (2×). The organic phase was dried over magnesium sulfate, filtered and concentrated to give a foam (9.88 g). Recrystallization (chloroform/ethyl acetate) gave crystals (6.87 g) of the E-isomer. m.p. 184°-185° C.

$^1$H NMR (CDCl$_3$, 400 MHz) δ 7.36-8.04 (m, 7H, ArH), 10.9 (s, 1H, CHO).

Analysis Calculated ($C_{15}H_9NO_3S$): C, 63.59; H, 3.20; N, 4.94. Found: C, 63.32; H, 2.98; N, 4.92.

EXAMPLE 4

5-[2-Hydroxy-1,2-diphenylethylidene]-2,4-thiazolidinedione

5(2-Hydroxy-1-phenylethylidene)-2,4-thiazolidinedione was prepared by the procedure of Example 1 from 2,4-thiazolidinedione and 2-bromoacetophenone.

M.P. 175°-176° C.

IR (KBr): 3370 (bd s), 1733 (s), 1690 (s), 1609 (s), 1329 (s), 1184 (s), 830 (m), 815 (m) cm$^{-1}$.

MS (EI) m/e (relative intensity): 235 (M$^+$, 43), 206 (100), 192 (9), 135 (48), 134 (74).

$^1$H NMR (acetonitrile-d$_3$): δ 4.92 (s,—CH$_2$OH,2H), 7.32-7.54 (m, ArH, 5H).

Analysis Calculated ($C_{11}H_9NO_3S$): C, 56.16; H, 3.86; N, 5.95. Found: C, 56.20; H, 3.91; N, 6.00.

5-(2-Hydroxy-1-phenylethylidene)-2,4-thiazolidinedione was converted to 5-(2-oxo-1-phenylethylidene)-2,4-thiazolidinedione by the procedure of Example 3. m.p. 168°-169° C.

MS (EI) m/e (relative intensity): 233 (M$^+$, 13), 205 (14), 134 (100).

$^1$H NMR (DMSO-d$_6$, 400 MHz) δ 7.2-7.5 (m, 5H, ArH), 10.7 (s, 1H, —CHO).

Analysis Calculated ($C_{11}H_7NO_3S$): C, 56.64; H, 3.02; N, 6.00. Found: C, 56.64; H, 3.19; N, 6.27.

To a solution of 5-(2-oxo-1-phenylethylidene)-2,4-thiazolidinedione in tetrahydrofuran (50 mL) at −78° C. was added phenylmagnesium chloride (11.7 mL, 2M, 23.4 mmol) dropwise over 5 min. After 5 min the reaction mixture was allowed to warm to 25° C. The reaction mixture was partitioned between 2N HCl and ether. The organic layer was dried over magnesium sulfate and concentrated to an oil. Chromatography (silica gel) followed by recrystallization (hexane/ether) gave the E-isomer as a white powder (10 g).

m.p. 96°-98° C.

IR (KBr): 3430 (bd), 1739 (s), 1682 (s), 1610 (w), 1600 (w), 1171 (m), 702 (s) cm$^{-1}$.

MS (EI) m/e (relative intensity): 311 (M$^+$, 26, 206 (100), 135 (21), 134 (32), 105 (73).

$^1$H NMR (DMSO-d$_6$, 400 MHz) δ 6.04 (d, J=3.6 Hz, 1 H, -CH-), 6.87 (d, J=7 Hz, 2 H, ArH), 7.16-7.36 (m, 8 H, ArH), 12.5 (bd s, 1 H, -NH).

Analysis Calculated ($C_{17}H_{13}NO_3S \cdot H_2O$): C, 61.99; H, 4.59; N, 4.25 Found: C, 63.30; H, 4.71; N, 4.25

EXAMPLE 5

5-[2-Hydroxy-1-(3,4-dichlorophenyl)ethylidene]-2,4-thiazolidinedione

The E-isomer of the title compound was prepared according to the procedure of Example 1 from 2,4-thiazolidinedione and 2,3',4'-trichloroacetophenone.

m.p. 186°-187° C.

IR(KBr): 3466 (bd), 1727 (s), 1701 (s), 1585 (m), 1468 (m), 1330 (m), 1170 (m) cm$^{-1}$.

MS (EI) m/e (relative intensity): 303 (M$^+$,23), 274 (36), 168 (63), 214 (51), 159 (100), 130 (51).

$^1$H NMR (DMSO-d$_6$, 400 MHz) δ 4.95 (d, J=5.6 Hz, 2H, —CH$_2$—), 5.11 (t, J=5.6 Hz, 1H, —OH), 7.3-7.8 (m, 3H, ArH).

Analysis Calculated ($C_{11}H_7Cl_2NO_3S$): C, 43.44; H, 2.32; N, 4.60. Found: C, 43.27; H, 2.58; N, 4.49.

EXAMPLE 6

5-[2-Oxo-1-(3,4-dichlorophenyl)-ethylidene]-2,4-thiazolidinedione (E)-5-[2-Hydroxy-1-(3,4-dichlorophenyl)ethylidine]-2,4-thiazolidinedione was converted to (E)-5-[2-oxo-1-(3,4-dichlorophenyl)-ethylidene]-2,4-thiazolidinedione by the procedure of Example 3.

m.p. 186°–187° C.

IR (KBr): 3307 (bd), 1751 (m), 1671 (s), 1560 (m), 1241 (m), 791 (m) cm$^{-1}$.

MS (EI) m/e (relative intensity): 301 (M+, 6), 204 (22), 202 (32).

$^1$H NMR (DMSO-d$_6$, 400 MHz) δ 7.30 (dd, J=1.9, 8.3 Hz, 1H, ArH), 7.58 (d, J=1.9 Hz, 1H, ArH), 7.76 (d, J=8.3 Hz, 1H, ArH), 10.68 (s, 1H, —CHO).

Analysis Calculated (C$_{11}$H$_5$Cl$_2$NO$_3$S): C, 43.74; H, 1.67; N, 4.64. Found: C, 43.44; H, 2.00; N, 4.57.

EXAMPLE 7

5-[2-Hydroxy-1-phenylpropylidene]-2,4-thiazolidinedione

The Z-isomer of the title compound was prepared from 2,4-thiazolidinedione and 2-bromopropiophenone according to the procedure of Example 1.

m.p. 199°–200° C.

IR (KBr): 3465 (bd), 1719 (s), 1675 (s), 1610 (m), 1310 (s), 1168 (m), 750 (m) cm$^-$.

MS (CI) m/e (relative intensity): 250 (M+H, 100), 232 (74), 161 (72).

$^1$H NMR (DMSO-d$_6$, 400 MHz) δ 1.08 (d, J=6.67 Hz, 3H, -CH$_3$), 4.4–4.5 (m, 1H, —CH—), 6.0 (d, J=3.5 Hz, 1H, —OH), 7.1–7.4 (m, 5H, ArH).

Analysis Calculated (C$_{12}$H$_{10}$NO$_3$S): C, 58.07; H, 4.06; N, 5.64. Found: C, 57.91; H, 4.05; N, 5.69.

EXAMPLE 8

5-[2-Hydroxy-1-(naphthalenyl)ethylidene]-3-methyl-2,4-thiazolidinedione (E)-5-[2-Hydroxy-1-(1-naphthalenyl)ethylidene]-2,4-thiazolidinedione (1.49 g, 5.22 mmol) was added to suspension of potassium carbonate (7.22 g, 52.2 mmol) in acetone. After 30 minutes iodomethane (0.65 mL, 10.4 mmol) was added. After 30 min the mixture was filtered, and concentrated to give a brown oil which was dissolved in chloroform. The resulting solution was washed with water then dried over magnesium sulfate and concentrated in vacuo to give an oil which was chromatographed on silica gel (chloroform/acetonitrile) to give a glass (1.17 g). Recrystallization from carbon tetrachloride/hexane/ether gave analytically pure E isomer of the title compound as yellow needles (0.90 g).

m.p. 112°–113° C.

IR (KBr): 3520 (bd), 1735 (s), 1668 (s), 1592 (m), 1367 (s), 1140 (m), 777 (s) cm$^{-1}$.

MS (EI) m/e (relative intensity): 299 (M+ 100), 270 (44), 213 (15), 196 (19), 185 (31), 153 (39), 152 (66), 141 (44), 128 (40).

$^1$H NMR (DCDl$_3$, 400 MHz): δ 3.26 (s, 3H, —NCH$_3$), 4.47 (dd, J=8.9, 6.7 Hz, 1H, —OH), 4.74 (dd, J=14.6, 8.9 Hz, 1H, —CHH—), 4.87 (dd, J=14.6, 6.7 Hz, 1H, —CHH—), 7.34–7.94 (m, 7H, ArH).

Analysis Calculated (C$_{16}$H$_{13}$NO$_3$S): C, 64.17; H, 4.34; N, 4.68. Found: C, 64.08; H, 4.51; N, 4.61.

EXAMPLE 9

5-[2-Methoxy-1-(naphthalenyl)ethylidene]-2,4-thiazolidinedione (E)-5-[2-Hydroxy-1-(1-naphthalenyl)ethylidene]-2,4-thiazolidinedione (1.50 g) was dissolved in tetrahydrofuran (25 mL) and treated with Hunig's base (1.41 mL). After 10 min 2-(trimethylsilyl)ethoxymethyl chloride (1.0 mL) was added. After 1 h aqueous hydrochloric acid (1.0N) was added and the tetrahydrofuran removed in vacuo. The aqueous phase was washed with ether and the ether phase washed with aqueous hydrochloric acid (1.0N) (2×) and 5% aqueous sodium bicarbonate (3×). The ether phase was dried over magnesium sulfate and concentrated in vacuo to give (E)-5-[2-hydroxy-1-(naphthalen-1-ylethylidene]-3-[2-(trimethylsilanyl)ethoxymethyl]-2,4-thiazolidenedione as an orange oil.

$^1$H NMR (CDCl$_3$, 200 MHz) δ −0.03 (s, 9H, —Si(CH$_3$)$_3$), 0.97 (t, J=8 Hz, 2H, —OCH$_2$CH$_2$—), 3.68 (t, J=8 Hz, 2H, —OCH$_2$CH$_2$—), 4.28 (t, J=7 Hz, 1H, —OH), 4.64–4.96 (m, 2H, —CH$_2$OH), 5.11 (s, 2H, NCH$_2$O), 7.3–8.0 (m, 7.H, ArH).

The above material was dissolved in dichloromethane (25 mL) and treated with triethylamine (1.1 mL). The mixture was cooled to −78° C. and treated with methanesulfonyl chloride (0.57 mL). After 1 h the reaction mixture was allowed to warm to 25° C. and washed with 1N aqueous hydrochloric acid (3×) and 5% aqueous sodium bicarbonate (3×). The organic layer was dried over magnesium sulfate and concentrated in vacuo to give methanesulfonic acid 2-{2,4-dioxo-3-[2-(trimethylsilanyl)ethoxymethyl]-thiazolidin-5-ylidene}-2-naphthalen-1-yl-ethyl ester E-isomer as a yellow oil.

$^1$H NMR (CDCl$_3$, 200 MHz) δ 0.0 (s, 9H, —Si(CH$_3$)$_3$), 0.98 (t, J=8 Hz, 2H, —OCH$_2$CH$_2$—), 2.67 (s, 3H, —SO$_2$CH$_3$), 3.68 (t, J=8 Hz, 2H, —OCH$_2$CH$_2$—), 5.12 (s, 2H, NCH$_2$O), 5.70 (d, J=13 Hz, 1H, —CHHOSO$_2$Me), 5.96 (d, J=13 Hz, 1H, —CHHOSO$_2$Me), 7.3–8.0 (m, 7H, ArH).

The above material was dissolved in methanol (50 mL) and heated at reflux for 1 h. Methanesulfonic acid (5 mL) was added and the resulting solution was heated at reflux for 6 h then cooled to 25° C. Aqueous potassium hydroxide (1.0N) was added until the mixture was basic. Methanol was removed in vacuo and the resulting mixture acidified with aqueous hydrochloric acid (2.0N). Extraction with ether (3×), drying of the combined ether layers with magnesium sulfate and concentration gave a yellow foam (1.29 g). Chromatography and recrystallization (hexane/ethyl acetate/ether) gave analytically pure (E)-5-[2-methoxy-1-(1-naphthalenyl)ethylidene]-2,4-thiazolidinedione as yellow crystals (0.38 g).

m.p. 133°–134° C.

IR (KBr): 3430 (bd), 3155 (m), 3019 (m), 1733 (s), 1683 (s), 1610 (m), 1323 (s), 1070 (m), 769 (s) cm$^{-1}$.

MS (EI) m/e (relative intensity): 299 (M+, 62), 222 (14), 213 (22), 196 (72), 195 (67), 183 (39), 165 (31), 152 (100), 139 (64).

$^1$H NMR (CDCl$_3$, 400 MHz): δ 3.29 (s, 3H, —OCH$_3$, 4.94 (d, J=14.0 Hz, 1 H, —CHH—), 5.14 (d, J=14.0 Hz, 1H, —CHH—), 7.3–8.0 (m, 7H, ArH), 8.42 (bd s, 1H, —NH).

Analysis Calculated (C$_{16}$H$_{13}$NO$_3$S): C, 64.17; H, 4.34; N, 4.68. Found: C, 64.22; H, 4.43; N, 4.65.

Pharmacology

On the morning of Day 1, 12–15 mice [male db/db (C57BL/KsJ), Jackson Laboratories, 2 to 7 months of age and body weight 35 to 60 g] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, the mice were randomly assigned into 3–5 groups (4–5 mice per group) of equivalent mean plasma glucose levels:

Group A: Vehicle control
Group B: Positive control (ciglitazone)
Group C: 1st Test drug
Group D: 2nd Test drug
Group E: 3rd Test drug.

On the afternoon of Days 1, 2 and 3 the vehicle, control or test drugs were administered (p.o.) to the ad libitum fed mice. The positive control, ciglitazone $\{(\pm)\text{-}5\text{-}[4\text{-}[(1\text{-methylcyclohexyl})\text{benzyl}]\text{thiazolidine-}2,4\text{-dione}$, Fujita et al., Diabetes 1983, 30, 804}, was given by gavage at a dose of 100 mg/kg/day. The test compounds were given by gavage at a dose of 100 mg/kg/day. The fourth and final dose was administered on the morning of day 4, after the mice had been fasted for 18 h. A blood sample was collected immediately preceding the last dose, followed by samples collected at 90 and 120 min after drug administration. Insulin is immediately administered to each mouse after the 120 min sample. Serial blood samples were collected at 45 and 120 min after insulin administration. The plasma was separated and the levels of glucose in plasma determined by the Abbot VP analyzer.

Analysis of variance followed by Dunnett's multiple comparison (one-sided) was used to estimate the degree of statistical significance of the difference between the vehicle control group and the individual drug-treated groups. A drug was considered active, at the specific dose administered, if the difference of the plasma glucose level has a $p<0.10$.

The actual difference between the mean percent change of blood glucose levels of the vehicle and the drug-treated group is reported in Table 1. Examination of the results tabulated in Table 1 shows that the compounds of this invention are well suited as antidiabetic agents for they lower blood glucose levels in diabetic (db/db) mice. For example, (E)-5-[2-oxo-1-(3,4-dichlorophenyl)ethylidene]-2,4-thiazolidinedione, the E-isomer of the compound of Example 6, effects a lowering of blood glucose levels comparable to that of ciglitazone at an identical dose of 100 mg/kg.

TABLE 1

| Compound of | Isomer | Blood Glucose Levels % Change From Vehicle (100 mg/kg) |
|---|---|---|
| Example 1 | E | −28 |
| Example 2 | E | −19 |
| Example 3 | E | −21 |
| Example 4 | E | −25 |
| Example 5 | E | −31 |
| Example 6 | E | −47 |
| Example 7 | Z | −23 |
| Example 8 | E | −27 |
| Example 9 | E | −24 |
| Ciglitazone | | −24 to −50 |

TABLE 1-continued

| Compound of | Isomer | Blood Glucose Levels % Change From Vehicle (100 mg/kg) |
|---|---|---|
| (Positive Control) | | |

Pharmaceutical Composition

Based on the results of the pharmacological assay, the compounds of this invention are useful in the treatment of hyperglycemia in diabetes mellitus.

The compounds may be administered neat or with a pharmaceutical carrier to a mammal in need thereof. The pharmaceutical carrier may be solid or liquid and the active compound shall be a therapeutically effective amount.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferable, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

What is claimed is:

1. A compound according to the formula:

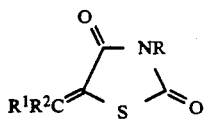

wherein:
R is H or lower alkyl,
$R^1$ is phenyl, 2,3-dichlorophenyl, naphthalenyl or 5-methyl-1-naphthalenyl;
$R^2$ is $R^3$—X— where X is —CO— or —CHOR$^4$— when X is CHOR$^4$, $R^3$ is H, lower alkyl, or aryl where aryl is phenyl or naphthalenyl, optionally substituted by halogen, lower alkyl or lower alkoxy and when X is —CO—, $R^3$ is H;
$R^4$ is H or methyl;
or a solvate or a pharmaceutically acceptable cationic salt thereof;
and $R^1$ and $R^2$ may be in the E or Z configuration with respect to the 2,4-thiazolindione ring.

2. A compound according to claim 1 wherein R is H or methyl,
$R^1$ is phenyl, 2,3-dichlorophenyl, naphthalenyl, or 5-methyl-1-naphthalenyl
$R^3$ is H, methyl or phenyl optionally substituted by halogen, lower alkyl or lower alkoxy; and
$R^4$ is H or methyl.

3. A compound according to claim 1 which is 5-[2-hydroxy-1-(1-naphthalenyl)ethylidene]-2,4-thiazolidinedione or a pharmaceutically acceptable salt thereof.

4. A compound according to claim 1 which is 5-[2-hydroxy-1-(5-methylnaphthalen-1-yl)ethylidene]-2,4-thiazolidinedione or a pharmaceutically acceptable salt thereof.

5. A compound according to claim 1 which is 5-[2-oxo-1-(1-naphthalenyl)ethylidene]-2,4-thiazolidinedione or a pharmaceutically acceptable salt thereof.

6. A compound according to claim 1 which is 5-[2-hydroxy-1,2-diphenylethylidene]-2,4-thiazolidinedione or a pharmaceutically acceptable salt thereof.

7. A compound according to claim 1 which is 5-[2-hydroxy-1-(3,4-dichlorophenyl)ethylidene]-2,4-thiazolidinedione or a pharmaceutically acceptable salt thereof.

8. A compound according to claim 1 which is 5-[2-oxo-1-(3,4-dichlorophenyl)ethylidene]-2,4-thiazolidinedione or a pharmaceutically acceptable salt thereof.

9. A compound according to claim 1 which is 5-[2-hydroxy-1-phenylpropylidene]-2,4-thiazolidinedione or a pharmaceutically acceptable salt thereof.

10. A compound according to claim 1 which is 5-[2-hydroxy-1-(1-naphthalenyl)ethylidene]-3-methyl-2,4-thiazolidinedione.

11. A compound according to claim 1 which is 5-[2-methoxy-1-(1-naphthalenyl)ethylidene]-2,4-thiazolidinedione.

12. A method of treating hyperglycemia in diabetes mellitus which comprises administration to a mammal in need thereof a therapeutically effective amount of a compound according to the formula:

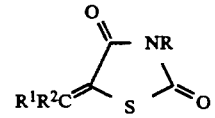

wherein:
R is H or lower alkyl,
$R^1$ is phenyl, 2,3-dichlorophenyl, naphthalenyl or 5-methyl-1-naphthalenyl;
$R^2$ is $R^3$—X— where X is —CO— or —CHOR$^4$— and when X is CHOR$^4$, $R^3$ is H, lower alkyl, or aryl where aryl is phenyl or naphthalenyl, optionally substituted by halogen, lower alkyl or lower alkoxy and when X is —CO—, $R^3$ is H;
$R^4$ is H or methyl;
or a solvate or a pharmaceutically acceptable cationic salt thereof;
and $R^1$ and $R^2$ may be in the E or Z configuration with respect to the 2,4-thiazolindione ring.

13. A method according to claim 12 where, in the compound used, R is H or methyl, $R^1$ is phenyl, 2,3-dichlorophenyl, naphthalenyl, or 5-methyl-1-naphthalenyl, $R^3$ is H, methyl or phenyl optionally substituted by halogen, lower alkyl or lower alkoxy; and $R^4$ is H or methyl.

14. A pharmaceutical composition for the treatment of hyperglycemia in diabetes mellitus which comprises a pharmaceutical carrier and a therapeutically effective amount of a compound having the formula:

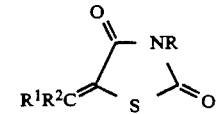

wherein:
R is H or lower alkyl,
$R^1$ is phenyl, 2,3-dichlorophenyl, naphthalenyl or 5-methyl-1-naphthalenyl;
$R^2$ is $R^3$—X— where X is —CO— or —CHOR$^4$— and when X is CHOR$^4$, $R^3$ is H, lower alkyl, or aryl where aryl is phenyl or naphthalenyl, optionally substituted by halogen, lower alkyl or lower alkoxy and when X is —CO—, $R^3$ is H;
$R^4$ is H or methyl;
or a solvate or a pharmaceutically acceptable cationic salt thereof;
and $R^1$ and $R^2$ may be in the E or Z configuration with respect to the 2,4-thiazolindione ring.

* * * * *